United States Patent [19]
Ueda

[11] Patent Number: 4,916,040
[45] Date of Patent: Apr. 10, 1990

[54] PHOTOSENSITIVE MEMBER WITH PHOTOCONDUCTIVE LAYER COMPRISING N-CYANOIMINE COMPOUND

[75] Inventor: Hideaki Ueda, Osaka, Japan

[73] Assignee: Minolta Camera Kabushiki Kaisha, Osaka, Japan

[21] Appl. No.: 388,512

[22] Filed: Aug. 2, 1989

[30] Foreign Application Priority Data

Aug. 2, 1988 [JP] Japan ........ 63-193218

[51] Int. Cl.[4] ........ G03G 5/06; G03G 5/14

[52] U.S. Cl. ........ 430/72; 430/73; 430/75; 430/78; 430/58; 430/59

[58] Field of Search ........ 430/72, 73, 75, 78, 430/58, 59

[56] References Cited

U.S. PATENT DOCUMENTS 4,045,220 8/1977 Contois et al. ........ 430/31
4,469,768 9/1984 Horie et al. ........ 430/58

FOREIGN PATENT DOCUMENTS 63-70257 3/1988 Japan .

*Primary Examiner*—J. David Welsh
*Attorney, Agent, or Firm*—Burns, Doane, Swecker & Mathis

[57] ABSTRACT

This invention relates to a photosensitive member wherein a photoconductive layer containing a N-cyanoimine compound represented by the following formula [I], [II] or [III] is formed on or over an electroconductive substrate;

[I]

[II]

[III]

wherein $R_1$-$R_{13}$ are respectively a hydrogen atom, an alkyl group, an alkoxy group, a halogen atom, a nitro group, a cyano group, a substituted sulfonyl group or a carboxylate group; n is an integer of 0-4; Z is a residual group which forms a ring with the benzene ring; Z may have a substituent; X is an oxygen atom or N-CN.

24 Claims, 1 Drawing Sheet

PHOTOSENSITIVE MEMBER WITH PHOTOCONDUCTIVE LAYER COMPRISING N-CYANOIMINE COMPOUND

BACKGROUND OF THE INVENTION

This invention relates to a photosensitive member containing a new N-cyanoimine compound.

Known photosensitive materials for forming a photosensitive member include inorganic photoconductive materials such as selenium, cadmium sulfide or zinc oxide.

These photosensitive materials have many advantages such as low loss of charges in the dark, an electrical charge which can be rapidly dissipated with irradiation of light and the like. However, they have disadvantages. For example, a photosensitive member based on selenium is difficult to produce, has high production costs and is difficult to handle due to inadequate resistivity to heat or mechanical impact. A photosensitive member based on cadmium sulfide has defects such as its unstable sensitivity in a highly humid enviroment and loss of stability with time because of the deterioration of dyestuffs, added as a sensitizer, by corona charge and fading with exposure.

Many kinds of organic photoconductive materials such as polyvinylcarbazole and so on have been proposed. These organic photoconductive materials have superior film forming properties, are light in weight, etc., but inferior in sensitivity, durability and environmental stability compared to the aforementioned inorganic photoconductive materials.

Various studies and developments have been in progress to overcome the above noted defects and problems. A function-divided photosensitive member of a laminated or a dispersed type has been proposed, in which charge generating function and charge transporting function are divided by different layers or different dispersed materials. The function-divided photosensitive member can be a highly efficient photosensitive member in electrophotographic properties such as chargeability, sensitivity, residual potential, durability with respect to copy and repetition, because most adequate materials can be selected from various materials. Further, function-divided photosensitive members have high productivity and low costs, since they can be prepared by coating, and suitably selected charge generating materials can freely control a region of photosensitive wavelength. Illustrative examples of such charge generating materials are organic pigments or dyes such as phthalocyanine pigment, cyanine pigment, polycyclic quinone pigment, perylene pigment, perinone pigment, indigo dye, thioindigo dye, squarain compounds, etc., and inorganic materials such as selenium, selenium-arsenic, selenium-tellurium, cadmium sulfide, zinc oxide, amorphous silicon, etc.

However, photosensitive members, which satisfy general static property requirements, are not produced easily, and photosensitive members having more improved sensitivity are desired.

With respect to charge transporting materials and in function-divided photosensitive members, there are proposed hydrazone compounds, pyrazoline compounds, and other various compounds (for example, see Japanese Laid-open Patent No. 70257/1988, which discloses that the compound with the formula below;

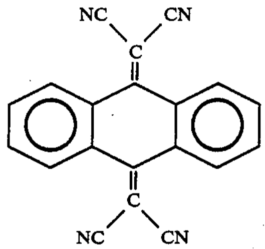

being different from a compound of the present invention, is used as a charge transporting material).

Further,positive holes or electrons are thought to be transported through a charge transporting layer, but with respect to electron transporting materials, an only mixture (1:1) of PVK (polyvinyl carbazole) with TNF (trinitrofluorenone) are put into practice. Therefore, in general, charge transporting materials are mainly positive-hole transportable. When charge transporting materials with positive hole-transportability are used in a photosensitive member, the photosensitive member must be charged negatively. The negative charges bring about another problem such that ozone deriorates a photosensitive member.

SUMMARY OF THE INVENTION

The object of the invention is to provide a new electron-transportable materials which can transport electrons efficiently and that also work as a sensitizer in a photosensitive member.

The present invention relates to a photosensitive member wherein a photoconductive layer containing a N-cyanoimine compound represented by the following formula [I], [II], or [III] is formed on or over an electroconductive substrate;

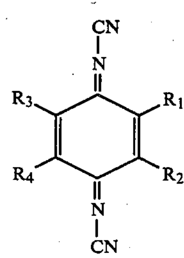

[I]

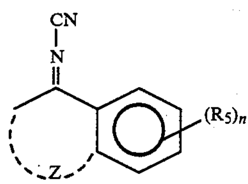

[II]

-continued

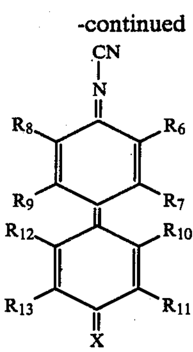

wherein $R_1$–$R_{13}$ are respectively a hydrogen atom, an alkyl group, an alkoxy group, a halogen atom, a nitro group, a cyano group, a substituted sulfonyl group or a carboxylate group; n is an integer of 0–4; Z is a residual group which forms a ring with the benzene ring; Z may have a substituent; X is an oxygen atom or N—CN.

DETAILED DESCRIPTION OF THE INVENTION

Figure 1:
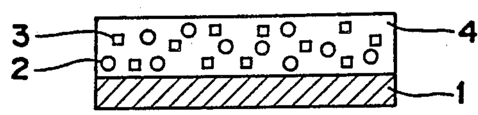
FIG. 1 is a diagram showing the structure of a dispersion-type photosensitive member embodying the invention comprising a photosensitive layer formed on an electrically conductive substrate.

The present invention provides a photosensitive member excellent in sensitivity, low residual potential and repetition stability.

The present invention has accomplished the above object by introduction of a specific N-cyanoimine compound into a photosensitive member.

The present invention provides a photosensitive member wherein a photoconductive layer containing a N-cyanoimine compound represented by the following formula [I], [II] or [III] is formed on or over an electroconductive substrate;

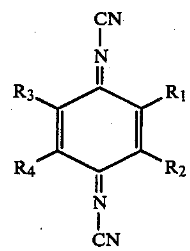

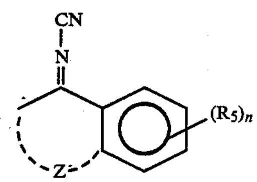

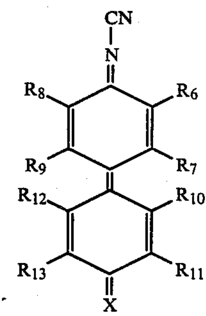

wherein $R_1$–$R_{13}$ are respectively a hydrogen atom, an alkyl group, an alkoxy group, a halogen atom, a nitro group, a cyano group, a substituted sulfonyl group or a carboxylate group; n is an integer of 0–4; Z is a residual group which forms a ring with the benzene ring; Z may have a substituent; X is an oxygen atom or N—CN.

Some of N-cyanoimine compounds represented by the general formula [I], [II] or [III] are per se known and may be prepared according to A. Aumüand S. Hüig, Lie bigs, Anm. Chem., 146-164 (1986).

For example, a N-cyano compound of [I] is prepared as below;

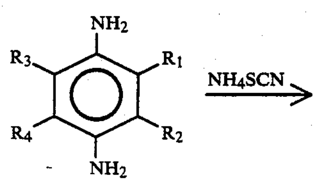

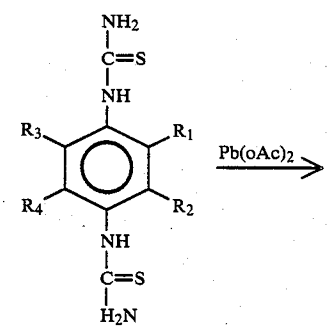

-continued

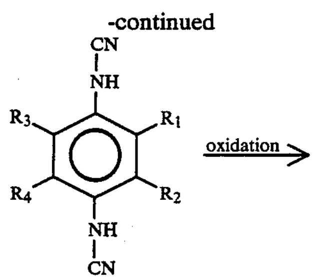

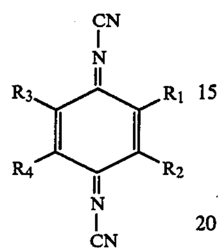

(wherein $R_1$–$R_4$ are same as aforementioned.)

As shown in the reaction formula above, a phenylene diamine compound is reacted with ammonium thiocyanato in an aqueous hydrochloric acid solution to give a bisthiourea compound. The bisthiourea compound is changed to a biscyanamide compound with the addition of lead acetate and potassium hydroxide in a boiling water.

Then, the biscyanamide compound is oxidized with manganese dioxide in toluene to obtain a N-cyano compound of [I].

$$\xrightarrow[\text{TiCl}_4]{\text{Me}_3\text{Si—N=C=N—SiMe}_3}$$

wherein $R_5$ is same as aforementioned.

As shown in the reaction formula above, a carbonyl compound is reacted for condensation with bis(trimethylsilyl)carbodiimide in the presence of catalyst of titanium tetrachloride in an inactive solvent such as dichloromethane.

A N-cyano compound of [III] is prepared as below;

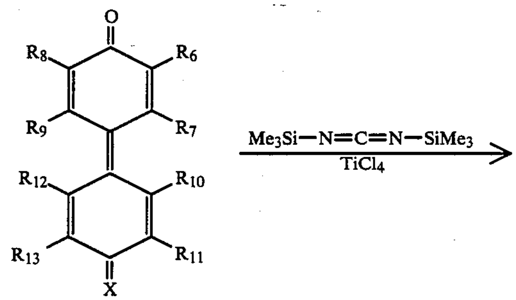

-continued

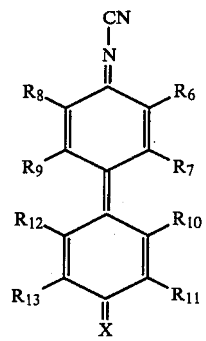

wherein $R_6$–$R_{13}$ are same as aforementioned.

As shown in the reaction formula above, a carbonyl compound is reacted for condensation with bis(trimethylsilyl)carbodiimide in the presence of catalyst of titanium tetrachloride in an inactive solvent such as dichloromethane.

A N-cyanoimine compound represented by the general formula [I], [II] or [III] is used to sensitize a photoconductive material or is incorporated in a charge transporting layer taking advantage only of excellent charge transporting ability when photosensitive member is of the laminated function-divided type, or in a photoconductive layer when the photosensitive member is of the single-layer dispersion type, to give excellent coating properties, excellent photographic properties such as charge-keeping ability, sensitivity and residual potential.

Examples of preferred N-cyanoimide compounds of the present invention represented by the formula (I) are those having the following structural formula. These examples are in no way limitative.

[1]

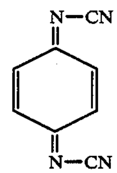

[2]

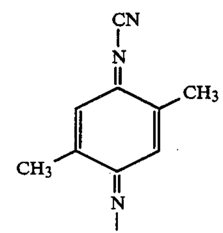

[3]

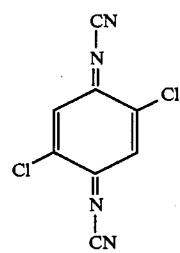

-continued
[4]
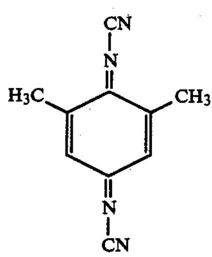
[5]
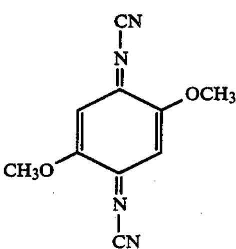
[6]
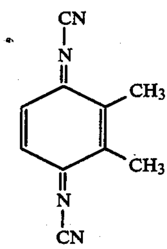
[7]
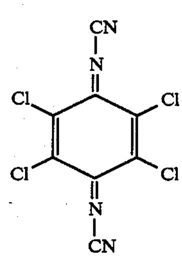
[8]
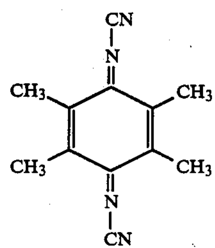
[9]
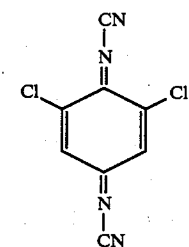
-continued
[10]
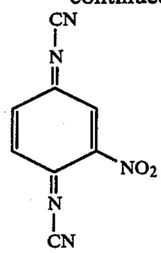
[11]
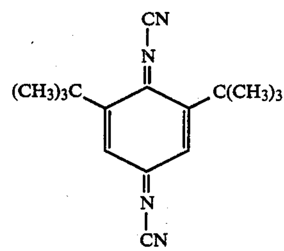
[12]
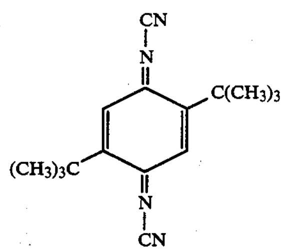
Examples of preferred N-cyanoimine compounds of the present invention represented by the formula [II] are those having the following structural formula. These examples are in no way limitative.
[13]
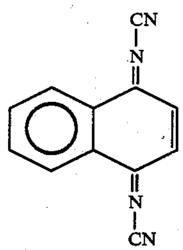
[14]
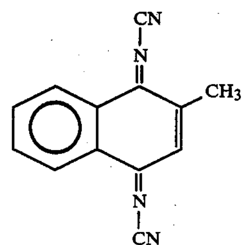
[15]
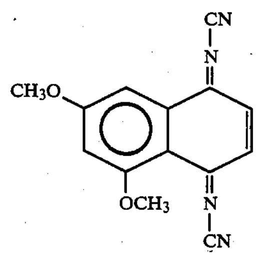

-continued
[16]
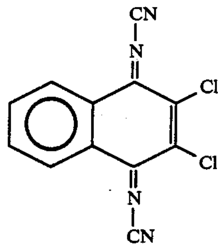
[17]
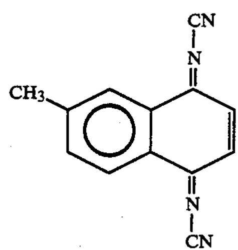
[18]
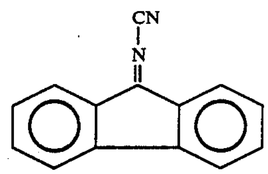
[19]
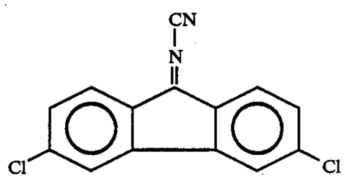
[20]
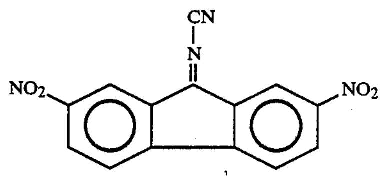
[21]
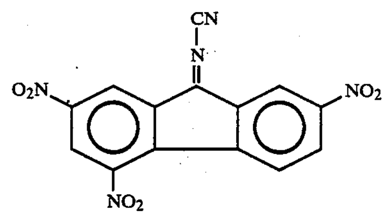
[22]
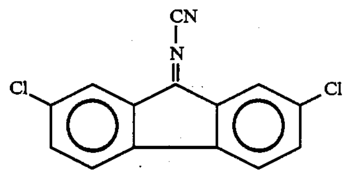
[23]
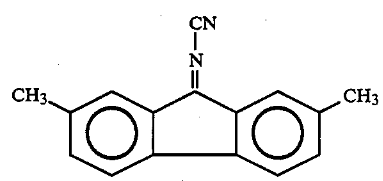
-continued
[24]
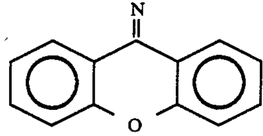
[25]
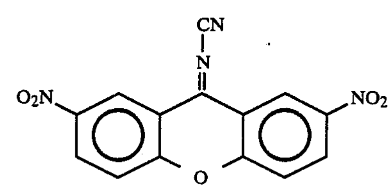
[26]
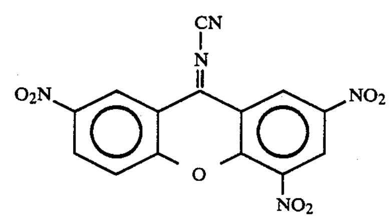
[27]
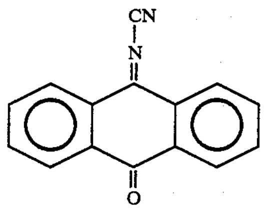
[28]
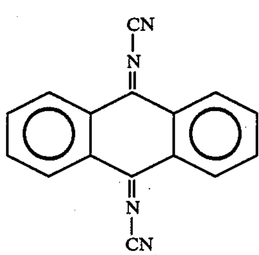
[29]
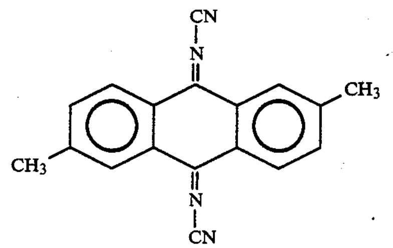
[30]
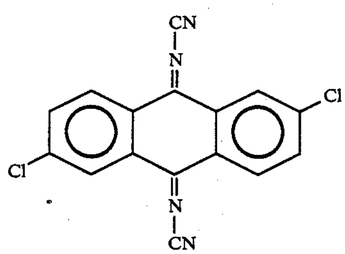

-continued
[31]
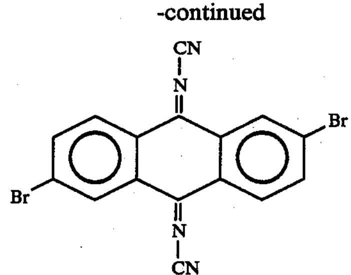
[32]
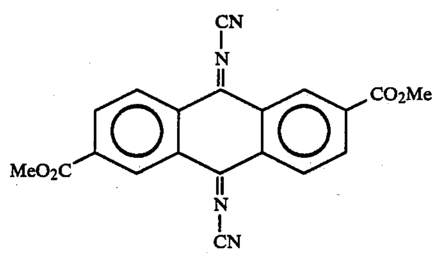
[33]
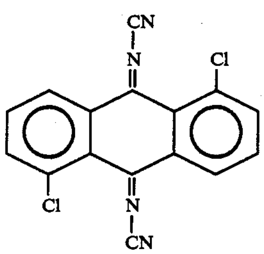
[34]
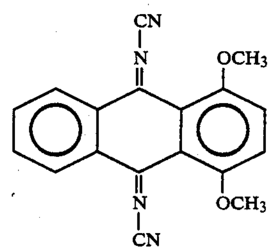
[35]
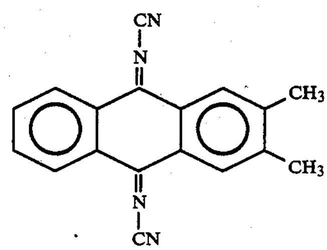
[36]
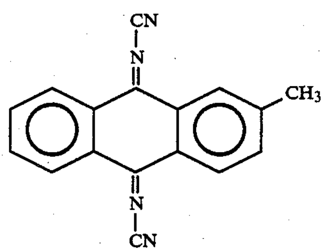
-continued
[37]
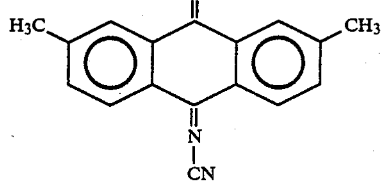
[38]
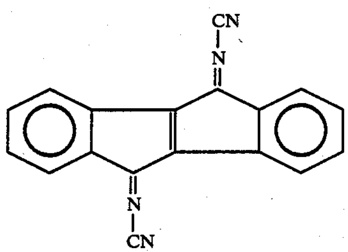
[39]
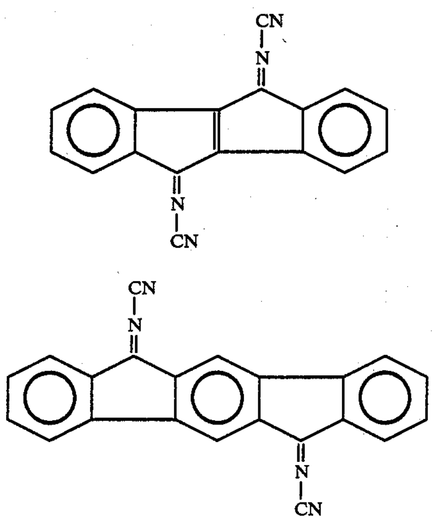
Examples of preferred N-cyanoimine compounds of the present invention represented by the formula [III] are those having the following structural formula. These examples are in no way limitative.
[40]
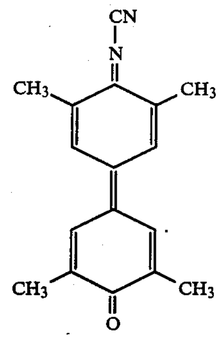
[41]
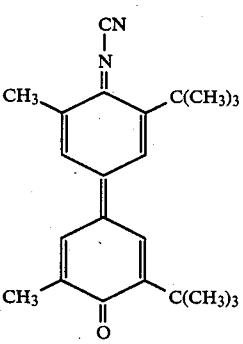

-continued

[42]

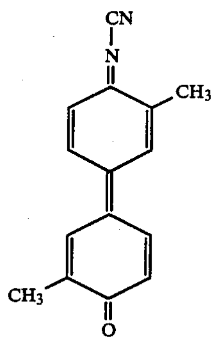

[43]

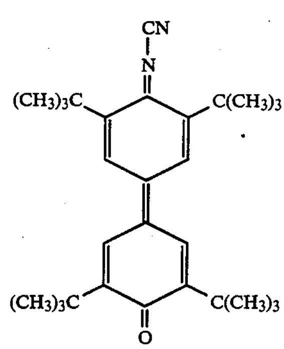

[44]

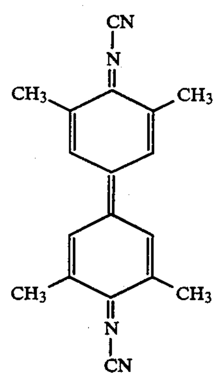

[45]

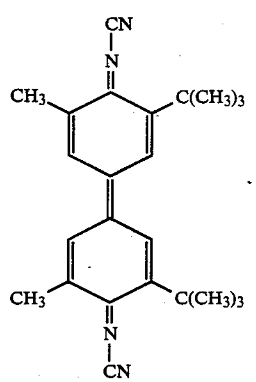

-continued

[46]

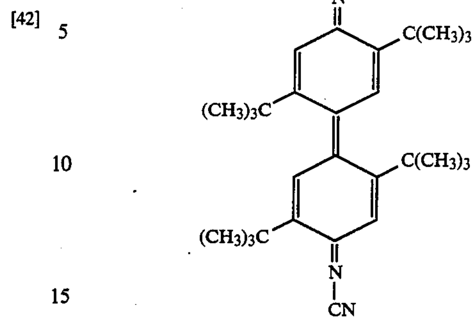

[47]

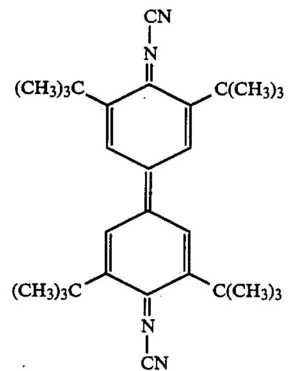

[48]

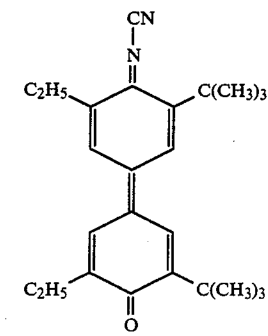

[49]

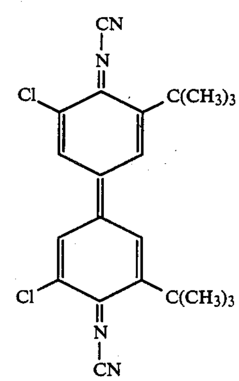

Those N-cyanoimine compounds may be used singly or in combination thereof.

FIGS. 1 to 5 schematically show examples of electrophotographic photosensitive members prepared with use of the N-cyanoimine compound of the invention.

FIG. 1 shows a photosensitive member comprising a photoconductive layer 4 formed on a substrate 1 and prepared from a charge generating material 3 and a charge transporting material 2 as admixed with a binder. The N-cyanoimine compound of the invention is used as the charge transporting material.

Figure 2:
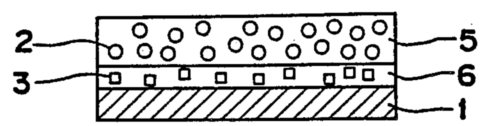
FIG. 2 is a diagram showing the structure of a photosensitive member of the function-divided type comprising a charge generating layer and a charge transporting layer which are formed on an electrically conductive substrate.

FIG. 2 shows a photosensitive member of the function-divided type comprising a charge generating layer 6 and a charge transporting layer 5 which are combined to serve as a photoconductive layer. The charge transporting layer 5 is formed on the surface of the charge generating layer 6. The N-cyanoimine compound of the invention is incorporated in the charge transporting layer 5.

Figure 3:
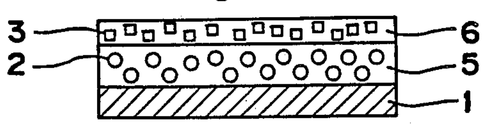
FIG. 3 is a diagram showing the structure of a member of another photosensitive member of the function-divided type comprising a charge generating layer and a charge transporting layer which are formed on an electrically conductive substrate.

FIG. 3 shows another photosensitive member of the function-divided type which, like the one shown in FIG. 2, comprises a charge generating layer 6 and a charge transporting layer 5. In converse relation to the member shown in FIG. 2, the charge generating layer 6 is formed on the surface of the charge generating layer 5.

Figure 4:
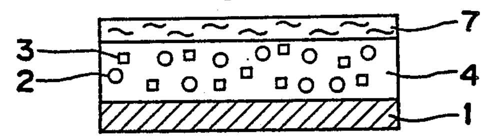
FIG. 4 is a diagram showing the structure of another dispersion-type photosensitive member comprising a photoconductive layer and a surface protective layer formed on an electrically conductive substrate.

The member shown in FIG. 4 comprises the one shown in FIG. 1 and a surface protective layer 7 formed on the surface of the photoconductive layer 4. The photoconductive layer 4 may be separated into a charge generating layer 6 and a charge transporting layer 5 to provide a photosensitive member of the function-divided type.

Figure 5:
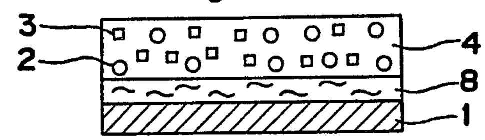
FIG. 5 is a diagram showing the structure of another dispersion-type photosensitive member comprising a photoconductive layer and an intermediate layer formed on an electrically conductive substrate.

FIG. 5 shows a photosensitive member having the same construction as the one shown in FIG. 1 except that an intermediate layer 8 is interposed between the substrate 1 and the photoconductive layer 4. The intermediate layer 8 serves to give enhanced adhesion, afford improved coatability, protect the substrate and assure injection of charges from the substrate into the photoconductive layer with improved effectiveness. Polyimide resin, polyester resin, polyvinyl butyral resin, casein, etc. are useful for forming the intermediate layer. The photoconductive layer of the member may also be modified to the function divided type.

A N-cyanoimine compound may be also added as a sensitizer for a photoconductive material, or a charge transporting material. Further N-cyanoimine compound may be modified to be used as a CT complex compound (electron donor).

The photosensitive member of the dispersion type having the same structure as the member of FIG. 1 described, i.e. having a photoconductive layer on an electrically conductive substrate, is prepared by dispersing a finely divided charge generating material in a solution of the N-cyanoimine compound and a binder resin, coating the conductive substrate with the dispersion and drying the coating to form the photoconductive layer. The photoconductive layer thus formed is 3 to 30 μm, preferably 5 to 20 μm, in thickness. If the charge generating material is used in too small amount, lower sensitivity will result, whereas presence of an excess of the material leads to impaired chargeability or gives reduced strength to the photoconductive layer. It is desirable that the photoconductive layer contains the charge generating material in an amount of 0.01 to 2 parts by weight, more desirably 0.05 to 1 part by weight, per one part by weight of the binder resin. The amount of N-cyanoimine compound is preferably 0.01 to 2 parts by weight, more preferably 0.02 to 1.2 parts by weight, per one part by weight of the binder resin. The N-cyanoimine compound may be used conjointly with a high-molecular-weight a charge generating material, such as polyvinylcarbazole, which is serviceable as a binder in itself, or with some other charge transporting material such as hydrazone.

The photosensitive member of the function-divided type having the same structure as the member of FIG. 2 described, i.e. having a charge generating layer formed on an electrically conductive substrate and a charge transporting layer on the charge generating layer, can be prepared by coating the substrate with a charge generating material by vacuum deposition or by coating the substrate with a composition obtained by dispersing the material in a suitable solvent which may contain a binder resin dissolved therein when so required and drying the coating, to form the charge generating layer, and further coating this layer with a solution of the N-cyanoimine compound serving as a charge transporting material and binder resin in a suitable solvent.

The charge generating layer thus formed is 4 μm or less, preferably 2 μm or less in thickness, while the charge transporting layer is 3 to 30 μm, preferably 5 to 20 μm, in thickness. It is suitable that the charge transporting layer contains the N-cyanoimine compound in an amount of 0.2 to 2 parts by weight, more suitably 0.3 to 1.2 parts by weight, per one part by weight of the binder resin. The N-cyanoimine compound may be used in combination with some other charge transporting materials. When this material is a high-molecular-weight charge transporting material which itself is serviceable as a binder, the other binder can be dispensed with. The photosensitive member, like the one shown in FIG. 3, may be so constructed that the charge transporting layer is provided on the electrically conductive substrate, with the charge generating layer formed on the charge transporting layer.

When a N-cyanoimine compound of the present invention is used as a sensitizer for other charge transporting materials, it is contained at the content of 0.01–20 wt.%, preferably 0.01–5 wt.% on the basis of the charge transporting material. If the content is less than 0.01 wt.%, the sensitizing effects can not be obtained sufficiently. If the content is more than 20 wt.%, the chargeability is lowered.

When a N-cyanoimine compound of the present invention is used as a sensitizer for charge generating material, it is contained at the content of 0.01–20 wt.%, preferably 0.1–5 wt.% on the basis of the charge generating material. If the content is less than 0.01 wt.%, the sensitizing effects can not be obtained sufficiently. If the content is more than 20 wt.%, the chargeability is lowered.

Example of charge generating materials useful for the present photosensitive member of the function-divided type or the dispersion-type are organic substances such as bisazo pigments, triarylmethane dyes, thiazine dyes, oxazine dyes, xanthene dyes, cyanine coloring agents, styryl coloring agents, pyrylium dyes, azo pigments, quinacridone pigments, indigo pigments, perylene pigments, polycyclic quinone pigments, bisbenzimidazole pigments, indanthrone pigments, squalylium pigments and phthalocyanine pigments; and inorganic substances such as selenium, selenium-tellurium, selenium-arsenic, cadmium sulfide and amorphous silicon. Any other material is also usable insofar as it generates charge carriers very efficiently upon absorption of light.

When a charge generating layer is formed by vacuum deposition, phthalocyanines, for example, such as metal-free phthalocyanine, titanyl phthalocyanine, aluminium chlorophthalocyanine are used. When a charge generating layer is formed by dispersion method, bisazo pigments, for example, are used.

The binder to be used is any of known thermoplastic resins or thermosetting resins having electrically insulating properties, light-curable resins and photoconductive resins. Although not limitatitve, examples of suitable binders are thermoplastic binders such as saturated polyester resin, polyamide resin, acrylic resin, ethylene-vinyl acetate copolymer, ion-crosslinked olefin copolymer (ionomer), styrene-butadiene block copolymer, polyallylate, polycarbonate, vinyl chloride-vinyl acetate copolymer, cellulose ester, polyimide and styrol resin, theremosetting binders such as epoxy resin, urethane resin, silicone resin, phenolic resin, melamine resin, xylene resin, alkyd resin and thermosetting acrylic resin; light-curable resins; photoconductive resins such as poly-N-vinylcarbazole, polyvinylpyrene and polyvinylanthracene; etc. These binders are usable singly or in admixture. The electrically insulating resin is preferably at least $1\times10^{12}$ ohm-cm in volume resistivity. More preferably among the foregoing examples are polyester resin, polycarbonate and acrylic resin.

Suitable solvents for use in the preparation of the composition are exemplified by aliphatic hydrocarbon halide such as carbon tetrachloride, dichloromethane, dichloroethane, dichloropropane, chloroform, trichloroethane; ketones such as cyclohexanone, methyl ethyl ketone, methyl isobutyl ketone, 2-methoxy-2-cyclopentanone; cyclic ethers such as dioxan, tetrahydrofuran, dioxolan, 4-methyl dioxolan, dimethyl dioxan; and a mixture thereof.

A N-cyanoimine compound of the invention has excellent dissolution properties in the above-mentioned solvent, and it results well in coatability and photosensitivity.

A N-cyanoimine compound of the invention has also good compatibility with a binder resin, and it results well in photosensitivity.

In preparing electrophographic photosensitive media according to the present invention, the binder may be used conjointly with plasticizers such as paraffin halide, polybiphenyl chloride, dimethylnaphthalene, dibutyl phthalate and o-terphenyl; election-attracting sensitizers such as chloranil, tetracyanoethylene, 2,4,7-trinitro-9-fluorenone, 5,6-dicyanobenzoquinone, tetracyanoquinodimethane, tetrachloroacetic anhydride and 3,5,-dinitrobenzoic acid; and sensitizers such as Methyl Violet, Rhodamine B, cyanine dye, pyrylium salt and thiapyrylium salt.

The photosensitive member thus prepared for use in electrophotography may have an adhesion or intermediate layer, or a surface protective layer when so required as already stated with reference to FIG. 4 or 5.

An intermediate layer is formed with polymer itself such as polyimide, polyamide, nitrocellulose, polyvinylbutyral, polyvinylalcohol, or formed by dispersing materials with low electrical resistance such as tin oxide or indium oxide, or by depositing aluminium oxide, zinc oxide, silicon oxide and so on.

The desirable thickness of an intermediate layer is 1 μm or less.

It is suitable that a surface protective layer is formed with polymer itself such as acrylic resin, polyaryl resin, polycarbonate resin, urethane resin, or formed by dispersing materials with low electrical resistance such as tin oxide or indium oxide. An organic plasma-polymerized polymer layer may be applied to the surface protective layer. The organic plasma-polymerized polymer layer, if necessary, may incorporate oxygen, halogen, atoms of the group III in the periodic table, or atoms of the group V in the periodic table. The desirable thickness of a surface protective layer is 5 μm or less.

As described above, a N-cyanoimine compound of the present invention is easy to prepare, can be incorporated into photosensitive member of the function-divided type or dispersion type and is usable in combination with various charge generating materials and charge transporting materials and, if desired, usable as a sensitizer. Further, the electrophotographic photosensitive member having the present N-cyanoimine compound incorporated therein can be charged negatively or positively and is very easy to produce, and exhibits improved sensitivity and is diminished in surface potential variations.

The present invention is explained with Examples hereinafter.

"Part" means "part by weight" in following Examples so long as it is particularly specified.

EXAMPLE 1

The bisazo compound represented by the following formula (A);

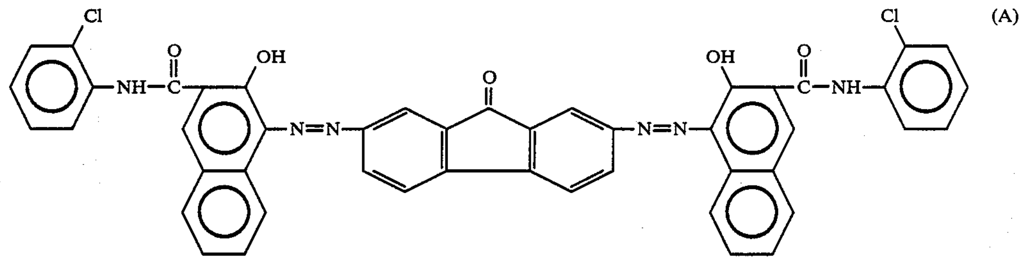

of 0.45 part by weight and 0.45 part by weight of polyester resin (Vylon 200 made by Toyobo K. K.) and 50 parts by weight of cyclohexanone were taken in Sand grinder for dispersion. The dispersion solution of the bisazo pigment was applied onto aluminotype-Mylar of 100 μm in thickness by a film applicator to form a charge generating layer so that a thickness of the layer after dried might be 0.3 g/m². A solution of 70 parts of the hydrazone compound represented by the following formula (B), 0.1 part of N-cyanoimine compound (20) and 70 parts of polycarbonate resin (K-1300; made by Teijin Kasei K. K.) dissolved in 400 parts of 1,4-dioxane was applied onto

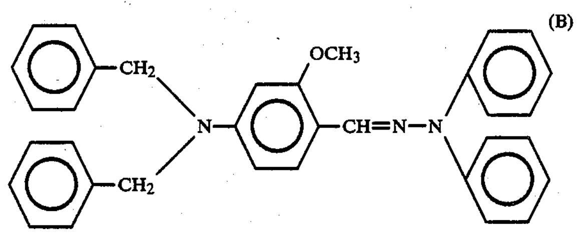

the above formed charge generating layer to form a charge transporting layer so that the thickness of the layer after dried might be 16 μm. Thus, a photosensitive member with the two layers was prepared.

EXAMPLE 2-3

Photosensitive members were prepared with the same structure and in a manner similar to Example 1 except that the N-cyanoimine compound (4), (8) were used respectively instead of the N-cyanoimine compound (20).

EXAMPLE 4

One part of the perylene compound represented by the following formula (C);

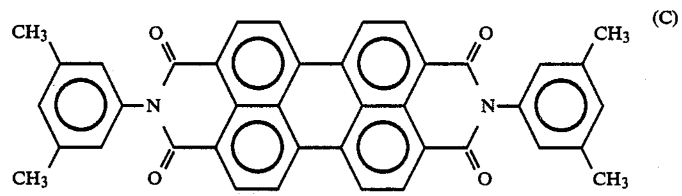

3 parts of PVK (polyvinylcarbazole) and 0.1 part of the N-cyanoimine compound (20) and 0.2 parts of polyester resin and 50 parts of a solvent mixture (1:1) of toluene with dioxane were taken in paints conditioner for dispersion. The dispersion solution was applied onto aluminotype-Mylar of 100 μm in thickness by a wire bar to form a monolayer type photosensitive member so that a thickness of the layer after dried might be 10 μm.

EXAMPLES 5-6

Photosensitive members were prepared with the same structure and in a manner similar to Example 4 except that the N-cyanoimine compounds (16) and (28) were used respectively instead of the N-cyanoimine compound (20).

Example 7

Titanylphthalocyanine (0.3 parts), 0.3 parts of polyvinyl butyral and 150 parts of cyclohexanone were taken in Sand grinder for dispersion. The dispersion solution was applied onto aluminotype-Mylar of 100 μm in thickness by a film applicator to form a charge generating layer so that a thickness of the layer after dried might be 0.3 g/m². A solution of 1 part of N-cyanoimine compound (25), 0.3 parts of p-diethylaminobenzaldehyde-N,N-diphenylhydrazone and 1 part of polycarbonate resin dissolved in 20 parts of dichloromethane was applied onto the above formed charge generating layer to form a charge transporting layer so that the thickness of the layer after dried might be 20 μm. Thus, a photosensitive member with the two layers was prepared.

EXAMPLES 8-9

Photosensitive members were prepared with the same structure and in a manner similar to Example 7, except that the N-cyanoimine compound (35) and (36) were used respectively instead of the N-cyanoimine compound (25).

EXAMPLE 10

A solution of 2 parts of polyvinylcarbazole and 3.4 parts of N-cyanoimine compound (21) dissolved in 16 parts of tetrahydrofuran was applied onto aluminotype-Mylar to form a monolayer type photosensitive member so that a thickness of the layer after dried might be 10 μm.

EXAMPLE 11

One part of polycyclic quinone represented by the following formula (D);

(D)

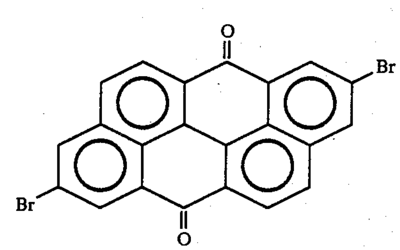

0.01 parts of N-cyanoimine compound (28), one part of polyester resin (Vylon 200 made by Toyobo K. K.) and 100 parts of cyclohexanone were taken in Sand mill for dispersion.

The obtained dispersion solution of the polycyclic quinone compound was applied onto a drum (80 ϕ) made of aluminium to form a charge generating layer so that a thickness of the layer after dried might be 0.3 g/m².

A solution of 70 parts of 1,1-bis(p-diethylaminophenyl)-4,4-diphenyl-1,3-butadiene and 70 parts of polycarbonate (K-1300; made by Teijin Kasei K. K.) dissolved in 400 parts of tetrahydrofuran was applied onto the above formed charge generating layer to form a charge transporting layer so that the thickness of the layer after dried might be 20 μm. Thus, a photosensitive member with two layers was prepared.

EXAMPLE 12

Titanylphthalocyanine (0.45 part), 0.45 parts of butyral resin (BX-1; made by Sekisui Kagaku Kogyo K. K.) 50 parts of dichloroethane were taken in sand mill for dispersion.

The dispersion solution was applied onto aluminotype Mylar of 100 μm in thickness by a film applicator to form a charge generating layer so that a thickness of the layer after dried might be 0.3 g/m².

A solution of 40 parts of N-cyanoimine compound (12) and 60 parts of polycarbonate resin (PC-Z; made by Mitsubishi Gass Kagaku K. K.) dissolved in 400 parts of dichloromethane was applied onto the above formed charge generating layer so that the thickness of the layer after dried might by 20 μm.

Thus, a photosensitive member with the two layers were prepared.

EXAMPLES 13-15

Photosensitive members were prepared in a manner similar to Example 12, except that N-cyanoimine compounds (41), (43) and (45) were used instead of the N-cyanoimine compound (12).

COMPARATIVE EXAMPLE 1

A photosensitive member was prepared in a manner similar to Example 1 except that the N-cyanoimine compound was not added.

COMPARATIVE EXAMPLE 2

A photosensitive member was prepared in a manner similar to Example 4 except that the N-cyanoimine compound was not added.

COMPARATIVE EXAMPLE 3

A photosensitive member was prepared in a manner similar to Example 7 except that anthraquinodimethane was used instead of the N-cyanoimine compound.

The photosensitive members prepared in Examples 1-3, 10, 11 were incorporated into a commercial electrophotographic copying machine (EP-470Z, product of Minolta Camera K. K.) and tested with application of a voltage of −6 Kv to the d.c. power supply and the photosensitive members prepared in Examples 4-9, 12-15 were tested with application of a voltage of +6 Kv to the d.c. power supply in the copying machine converted for positive charging to measure the initial surface potential Vo (V), the amount of exposure required for Vo to reduce to half of $V_0$ ($E\frac{1}{2}$ (lux·sec)), and the potential decay rate $DDR_1$ (%) when the member was allowed to stand in the dark for 1 second after charging.

The results are shown in Table 1.

TABLE 1

| | $V_o$ (V) | $E\frac{1}{2}$ (lux · sec) | $DDR_1$ (%) | $V_R$ (V) |
|---|---|---|---|---|
| Example 1 | −650 | 1.2 | 5.0 | −3 |
| Example 2 | −660 | 1.4 | 4.3 | −5 |
| Example 3 | −650 | 1.4 | 4.7 | −5 |
| Example 4 | +620 | 4.2 | 8.5 | +10 |
| Example 5 | +630 | 4.5 | 8.0 | +11 |
| Example 6 | +630 | 4.3 | 8.2 | +10 |
| Example 7 | +640 | 1.0 | 5.7 | +2 |
| Example 8 | +650 | 1.2 | 5.0 | +3 |
| Exmaple 9 | +650 | 1.3 | 4.8 | +5 |
| Example 10 | −650 | 5.7 | 5.3 | −8 |
| Example 11 | −650 | 1.4 | 4.0 | −2 |
| Example 12 | +640 | 2.8 | 3.5 | +10 |
| Example 13 | +630 | 2.3 | 4.2 | +5 |
| Example 14 | +630 | 2.1 | 4.2 | +4 |
| Example 15 | +620 | 2.4 | 4.4 | +6 |
| Comparative Example 1 | −660 | 1.8 | 4.3 | −7 |
| Comparative Example 2 | +630 | 5.2 | 8.0 | +15 |
| Comparative Example 3 | +650 | 9.7 | 4.1 | +15 |

What is claimed is:

1. A photosensitive member wherein a photoconductive layer comprising a N-cyanoimine compound represented by the following formula [I], [II] or [III] is formed on or over an electroconductive substrate;

[I]

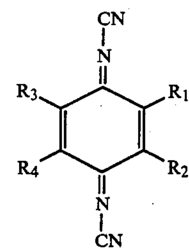

[II]

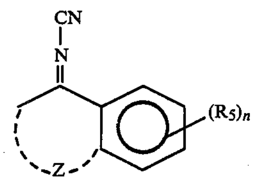

[III]

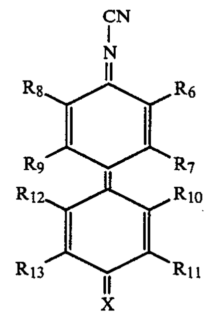

wherein $R_1$-$R_{13}$ are respectively a hydrogen atom, an alkyl group, an alkoxy group, a halogen atom, a nitro group, a cyano group, a substituted sulfonyl group or a carboxylate group; n is an integer of 0-4; Z is a residual group which forms a ring with the benzene ring; Z may have a substituent; X ix an oxygen atom or N—CN.

2. A photosensitive member of claim 1, wherein the photoconductive layer has a surface protective layer thereon.

3. A photosensitive member of claim 1, wherein an intermediate layer is interposed between the substrate and the photoconductive layer.

4. A photosensitive member of function divided type with a photoconductive layer comprising a charge generating layer and a charge transporting layer, said photoconductive layer comprising N-cyanoimine compound represented by the following formula [I], [II] or [III] is formed on or over an electroconductive substrate;

[I]

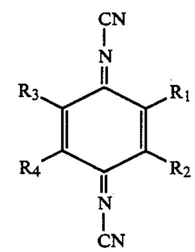

-continued

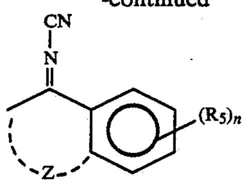

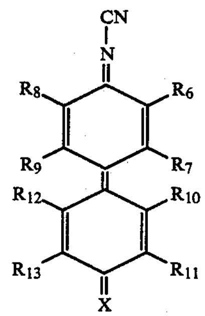

wherein $R_1$–$R_{13}$ are respectively a hydrogen atom, an alkyl group, an alkoxy group, a halogen atom, a nitro group, a cyano group, a substituted sulfonyl group or a carboxylate group; n is an integer of 0–4; Z is a residual group which forms a ring with the benzene ring; Z may have a substituent; X is an oxygen atom or N—CN.

5. A photosensitive member of claim 4, wherein the charge transporting layer contains the N-cyanoimine compound as a charge transporting material dispersed in a resin.

6. A photosensitive member of claim 5, wherein the N-cyanoimine compound is contained at the content of 0.2–2 parts by weight on the basis of one part by weight of the resin.

7. A photosensitive member of claim 5, wherein the N-cyanoimine compound is electrontransportable.

8. A photosensitive member of claim 4, wherein the charge transporting layer is 3–30 μm in thickness.

9. A photosensitive member of claim 4, wherein the charge transporting layer contains at least a charge transporting material and the N-cyanoimine compound as a sensitizer dispersed in a resin.

10. A photosensitive member of claim 9, wherein the charge transporting layer contains the N-cyanoimine compound at the content of 0.01–20 percents by weight on the basis of the charge transporting material.

11. A photosensitive member of claim 4, wherein the charge generating layer contains at least a charge generating material dispersed in a resin.

12. A photosensitive member of claim 4, wherein the charge generating layer is formed by depositing a charge generating material in vacuum.

13. A photosensitive member of claim 4, wherein the charge generating layer contains at least a charge generating material and the N-cyanoimine compound as a sensitizer dispersed in a resin.

14. A photosensitive member of claim 13, wherein the charge generating layer contains the N-cyanoimine compound at the content of 0.01–20 wt.% on the basis of the charge generating material.

15. A photosensitive member of claim 4, wherein the charge generating layer is formed on an electrically conductive substrate and the charge transporting layer is formed on the charge generating layer.

16. A photosensitive member of claim 4, wherein the charge transporting layer is formed on an electrically conductive substrate and the charge generating layer is formed on the charge transporting layer.

17. A photosensitive member of monolayer type comprising a photoconductive layer with a charge generating material dispersed in a resin, said photoconductive layer comprising a N-cyanoimine compound represented by the following formula [I], [II] or [III] is formed on or over an electroconductive substrate;

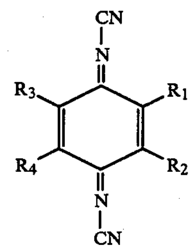

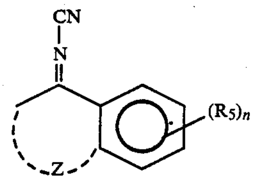

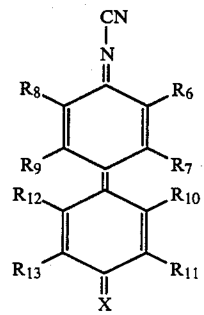

wherein $R_1$–$R_{13}$ are respectively a hydrogen atom, an alkyl group, an alkoxy group, a halogen atom, a nitro group, a cyano group, a substituted sulfonyl group or a carboxylate group; n is an integer of 0–4; Z is a residual group which forms a ring with the benzene ring; Z may have a substituent; X is an oxygen atom or N—CN.

18. A photosensitive member of claim 17, wherein the N-cyanoimine compound contained in the photoconductive layer functions as a sensitizer.

19. A photosensitive member of claim 18, wherein the N-cyanoimine compound is contained at the content of 0.01–20 percents by weight on the basis of a charge generating material.

20. A photosensitive member of claim 17, wherein the photoconductive layer contains a charge transporting material and the N-cyanoimine compound as a sensitizer.

21. A photosensitive member of claim 17, wherein the photoconductive layer contains the N-cyano-imine compound as a charge transporting material at the content of 0.2–2 parts by weight on the basis of one part of a resin.

22. A photosensitive member of claim 17, wherein the photoconductive layer contains an electron-donor which forms a CT complex with the N-cyanoimine compound.

23. A photosensitive member of claim 22, wherein the electron-donor is polyvinylcarbazole.

24. A photosensitive member of monolayer type, wherein a photoconductive layer comprising a N-cyanoimine compound represented by the following formula [I], [II] or [III], and an electron-donor which forms a CT complex with the N-cyanoimine compound is formed on or over an electroconductive substrate;

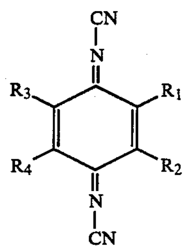

[I]

-continued

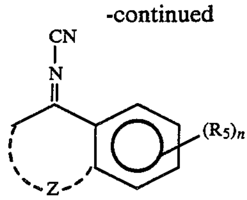

[II]

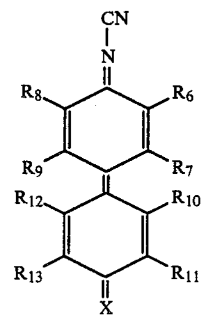

[III]

wherein $R_1$–$R_{13}$ are respectively a hydrogen atom, an alkyl group, an alkoxy group, a halogen atom, a nitro group, a cyano group, a substituted sulfonyl group or a carboxylate group; n is an integer of 0–4; Z is a residual group which forms a ring with the benzene ring; Z may have a substituent; X is an oxygen atom or N—CN.

* * * * *